(12) United States Patent
Tacconi (10) Patent No.: US 9,643,070 B2
(45) Date of Patent: May 9, 2017

(54) SYSTEM AND METHODS TO REMOTELY AND ASYNCHRONOUSLY INTERACT WITH REHABILITATION VIDEO-GAMES

(75) Inventor: David Tacconi, Trento (IT)

(73) Assignee: COREHAB S.R.L., Trento (IT)

(*) Notice: Subject to any disclaimer, the term of this patent is extended or adjusted under 35 U.S.C. 154(b) by 163 days.

(21) Appl. No.: 14/111,167

(22) PCT Filed: Mar. 22, 2012

(86) PCT No.: PCT/EP2012/055101
§ 371 (c)(1),
(2), (4) Date: Oct. 10, 2013

(87) PCT Pub. No.: WO2012/139868
PCT Pub. Date: Oct. 18, 2012

(65) Prior Publication Data
US 2014/0031098 A1    Jan. 30, 2014

(30) Foreign Application Priority Data

Apr. 11, 2011    (EP) .................................... 11161962

(51) Int. Cl.
*A63F 13/00* (2014.01)
*A63B 71/00* (2006.01)
(Continued)

(52) U.S. Cl.
CPC .... *A63B 71/0009* (2013.01); *A63B 21/00181* (2013.01); *A63B 24/0075* (2013.01);
(Continued)

(58) Field of Classification Search
CPC  A61B 5/00; A61B 5/112; A61N 1/361; A63F 13/12; A63F 13/212; A63F 13/67; G06F 19/3481; G06F 3/017
See application file for complete search history.

(56) References Cited

U.S. PATENT DOCUMENTS

2005/0240086 A1*  10/2005  Akay ................... A61B 5/0002
                                                                600/300
2008/0243038 A1   10/2008  Bennett
(Continued)

FOREIGN PATENT DOCUMENTS

JP          11008779        1/1999
WO    WO 2007/030947 A     3/2007

*Primary Examiner* — David L Lewis
*Assistant Examiner* — Eric M Thomas
(74) *Attorney, Agent, or Firm* — Davis, Malm & D'Agostine PC (57) ABSTRACT

The invention presents a system and methods to perform rehabilitation or physical therapy exercise while doing specifically designed video-games with the support of a therapist. Patient plays said video-games with external controllers with motion sensors connected to a pc or a laptop. The therapist can influence a gaming session of the patient by setting on a shared web-service thresholds for the patient. Said settings are gathered before starting a gaming session and patient movements are filtered by said settings to control the video-game. The patient is then limited in the movements by the feedbacks provided by the audio-visual interface of the video-game: movements on the screen are a result of the real movement done by the patient with said motion sensors filtered by the settings imposed by the therapist on the shared web space. On the other side, a patient with problems in doing some movements, can effectively play a video-game thanks to filtering imposed by the therapist. Information about the game played, and consequently about movements performed, are finally uploaded on the web-service for further analysis by the therapist.

5 Claims, 6 Drawing Sheets (51) Int. Cl.
*A63B 21/00* (2006.01)
*A63B 24/00* (2006.01)

(52) U.S. Cl.
CPC ....... *A63B 2220/16* (2013.01); *A63B 2220/40* (2013.01); *A63B 2220/52* (2013.01); *A63B 2220/803* (2013.01); *A63B 2225/20* (2013.01); *A63B 2225/50* (2013.01); *A63F 2300/535* (2013.01); *A63F 2300/558* (2013.01); *A63F 2300/5546* (2013.01)

(56) References Cited

U.S. PATENT DOCUMENTS

| | | | |
|---|---|---|---|
| 2009/0083070 A1* | 3/2009 | Giftakis | A61N 1/36132 705/2 |
| 2009/0107207 A1* | 4/2009 | Yamazaki | G01G 23/01 73/1.13 |
| 2009/0233769 A1* | 9/2009 | Pryor | B60K 35/00 482/8 |
| 2010/0125026 A1 | 5/2010 | Zavadsky | |
| 2010/0169110 A1* | 7/2010 | Sawano | A63F 13/12 705/2 |
| 2014/0153794 A1* | 6/2014 | Varaklis | A61B 5/1124 382/128 |

* cited by examiner

SYSTEM AND METHODS TO REMOTELY AND ASYNCHRONOUSLY INTERACT WITH REHABILITATION VIDEO-GAMES

BACKGROUND

The invention relates to improved systems and methods for supporting the use of video-games for rehabilitation, with a motion-sensing controller and an asynchronous interaction between a patient and a therapist. In particular, it relates to a scenario in which the patient is using said motion sensing controller to control a specifically designed video-game and the therapist is able to impose through remote settings some thresholds to limit the patient's movements.

Differently to any other previous invention, where some sensors and actuators limit the movement of the patient, in the present invention the movements of the patient are limited without interfering with the controller. Instead, the video-game reacts by filtering the output of the controllers (i.e. patient movement) with the therapist settings. Therefore the technical advantage is that the patient limits on his own the movements thanks to the audio-visual feedback of the video-game. A further advantage is that in this way the patient can play effectively a video-game, even if seriously injured, thanks to the filter imposed by therapist: this has the advantage of introducing entertainment in the rehabilitation process, making the patient more willing to undergo the rehabilitation session.

Furthermore, results and data about the exercise done through the use of video-games are periodically sent and stored for remote control by the therapist. Said bi-directional interaction is obtained through the use of a shared web service, accessible only by the therapist and the patient, where the therapist can set and adjust settings and where data on the games played, i.e. on the exercises done, can be analysed.

Said motion sensing controllers used by patients are devices that leverage on three dimensional accelerometers, gyroscope and weight measurement to sense a movement of an arm or a leg and on infrared communication between the controller itself and an infrared receiver posed close to the screen to determine the distance of the player from the screen; furthermore, said controllers have the capability to be connected to a laptop, a computer or a gaming console through standard communication protocols, such as Bluetooth, USB or RFCOMM. With such controllers, players are able to control a video-game through body movements. Said controllers can be composed by a plurality of devices each sensing the movement of a part of the body and connected among them via wireless or cable communications. Said motion sensing controllers include also boards able to sense precisely the weight of the player and the movement of the player with respect to the equilibrium axis, i.e. let the player control the game with a slight movement of the body with respect to the said axis.

In this invention, specific rehabilitation exercises are associated with simple video-games, to be controlled with movements of the body, attached to said motion sensing controllers that let the patient do a correct exercise for the related therapy.

The use of video-games for rehabilitation purposes are known in the art. For instance, U.S. Pat. No. 6,712,692 proposes the use of existing video-games for physical training and rehabilitation, and the input coming from game controllers are clustered in order to command the interaction with the video-game itself. The movements able to control the video-game are specifically designed for rehabilitation purposes.

In many works, the therapist can interact with the video-game synchronously, i.e. correct the patient movements while playing through the support of a video connection or by checking the output of the video-game in real-time, communicating then with the patient through a connection (internet or telephone). Through the same connection, information are stored remotely. This is the case of U.S. Pat. No. 6,918,858, where systems and methods for providing an improved exercise device with access to motivational programming over telephone communication connection lines are proposed. In US 2006/0277074 a computerized clinic system for rehabilitation is introduced. Information are remotely stored in said system and retrieved to avoid wasting of time for the patient when in the clinic or to determine a better usage of rehabilitation machines. In U.S. Pat. No. 6,458,060, systems and methods for interaction with special exercise device are presented: in particular, the object of the invention is to introduce such devices to simulate group exercise and synchronize with a program. In WO 2007113890, a rehabilitative model is proposed that implements traditional methods to enhance interaction between the patient and the provider of rehabilitative care or therapist, with recourse to computer systems connected via a network, through which it is made possible the intervention in support of other specialists, as well as remote control, by the competent health structures, of the results obtained at the patient's home. In WO 2007030947 an interface device for operative connection between a computer and a motion input system is described in order to let patients doing rehabilitation while playing with interactive videogames.

In addition, other inventions proposed system and methods to control user movements by changing resistance forces of a specifically designed hardware or machine, tailored to rehabilitation of a part of the body.

U.S. Pat. No. 6,313,000 shows a system for motivating and controlling patient's performance over the web for rehabilitating an arm or even another part of the body through the use of common hardware, such as a low cost joystick. The main innovation is given by the fact that multiple users can be controlled simultaneously and not in real time as soon as personalized information are downloaded onto the patient's device before starting a session. In this invention the therapist interacts asynchronously with the patient, and some settings are able to control the activities of a joystick or hardware, by influencing the movement of the controller itself.

This is also the case of US 2007/0299371 where a rehabilitation device able to guide patient movements is introduced. Such device learns from former movements of the patient or from therapist's motions and then reply it for the patient. In particular trajectories and forces are programmable.

WO02069609A2 presents a similar invention, where the forces are controlled through a robotic apparatus and a wireless connection with a sensor and an actuator on the rehabilitation device. The sensor provides data about what has been done, while the actuator is activated as a consequence of parsed data.

Furthermore, in U.S. Pat. No. 7,169,085, a system and method are introduced to generate prescription of exercise based on patient's assessment. In particular exercise protocols are generated by algorithm-based assessment completed by the user, including, but not limited to, movement and exercise useful to evaluate user capabilities. However, evaluated protocols are delivered to users through any communication means, and do not determine directly the way the patient interact with the rehabilitation device.

US 2010/0125026 discloses a game controller that can provide variable or adjustable resistance during strength training exercise in a training machine. The system may be used to enable automated physiotherapy. The system enables downloading parameters from a remote server, the parameters being set by a physiotherapist on the basis of the current status of the physiotherapy program of the patient.

Summary of the invention

The invention is a method and a system thereof for providing a personalized rehabilitation service to a patient with motion impairments by employing a gaming platform with motion sensors. The method comprises downloading rehabilitation parameters from a remote server, wherein the parameters are being set by a therapist on the basis of the current status of the rehabilitation program of the patient. According to the invention the parameters are modifying the output of said motion sensors of said gaming platform via a controller to determine a different audio-visual feedback of the gaming platform player movement so that the patient is forced to perform specific movements thanks to the audio-visual feedback of the gaming platform that are the result of a combination of patient movements and therapist parameter settings such that the usability of the game is unaltered by the impaired movement of the patient.

With the current invention, a therapist can interact asynchronously and remotely with the video-game of the patient by setting specific thresholds as for instance time of playing, amplitude of movements and weight on a part of the body. Such parameters influence the video-game output itself, and not a specifically designed hardware.

This has the remarkable advantage that no expensive tailored designed hardware is needed, but only software can control the effectiveness of the game via the settings of the therapist. Moreover, the can render the remote rehabilitation accessible to everyone thanks to the low cost and large availability of the gaming platforms. In particular, whenever a setting is decided by the therapist and saved on the shared web-service, it is gathered before the game starts and then it filters the output of the motion sensing controller and determines a different audio-visual feedback of the video-game to player movement. Said setting is for instance related to the maximum weight that a patient injured to the left leg can put on the leg itself: as soon as this weight threshold is reached, the video-game reacts as if the patient has put the maximum weight on the left side, by filtering the weight adding a quantity to the real measured value. At the same time, to reach the maximum movement on the video-game on the right side, the patient has to put the maximum weight on that part, because no settings have been imposed for that movement. This filtering of controller outputs allows patients to control naturally their movements on the injured part and keep the normal movement on the not-injured parts.

Information and data about patient movements, done while playing, are stored continuously on the shared web-space. Information are stored with respect to previous settings of the therapist, i.e. taking into account the thresholds specified for the game. The therapist can access such information at any time and decide on patient next settings according to what has been done.

For instance, a therapist can adjust said settings whenever a patient has finished a rehabilitation cycle or has successfully passed a medical exam or a periodical control, for instance increasing the threshold on the weight to be posed on the left leg for the cited example.

As said, after each gaming session, a report on the exercise done by the patient including the time spent doing rehabilitation and a synthesis of the movements done with said motion sensing controllers is sent and saved on the shared web-service. Such report is associated to the current part of the rehabilitation cycle and compared with the setting decided previously. In this way, the therapist has always a complete view of the rehabilitation done by the patient; on the contrary, the patient knows that a therapist is checking what is done so far, and he is somehow influenced to do rehabilitation more continuously.

BRIEF DESCRIPTION OF THE DRAWINGS

FIG. 2 Message exchange between patient and therapist through the web-service FIG. 3 Flow chart representing the filtering of information as decided by therapist settings before reaching the video-game output FIG. 4 Message exchange among modules to load therapist settings and filter output of Controller Interpreter to drive the gaming platform properly FIG. 5 Information uploaded on the web-service after gaming session FIG. 6 Information uploaded on the web-service and automatically generating new upload settings.

DETAILED DESCRIPTION OF THE INVENTION

The main aspects of the invention are the followings:
1. the first one is related to the filtering imposed to patient movement by therapist settings when patient plays a video-game. The patient is forced to perform some specific movements thanks to the audio-visual feedback of the video-game that will be the result of the combination of patient movements and therapist settings. Additionally, a patient with limited ability in doing certain movements will be able to play effectively a video-game, thanks to the combination of movements and specific settings.
2. The second aspect is related to the way information are stored on the shared web space while the patient is playing, with respect to therapist settings. This information help the therapist in understanding what the patient has done and decide new settings according to the history of patient movements coupled with the imposed settings, and the status of the rehabilitation programme.

Figure 1:
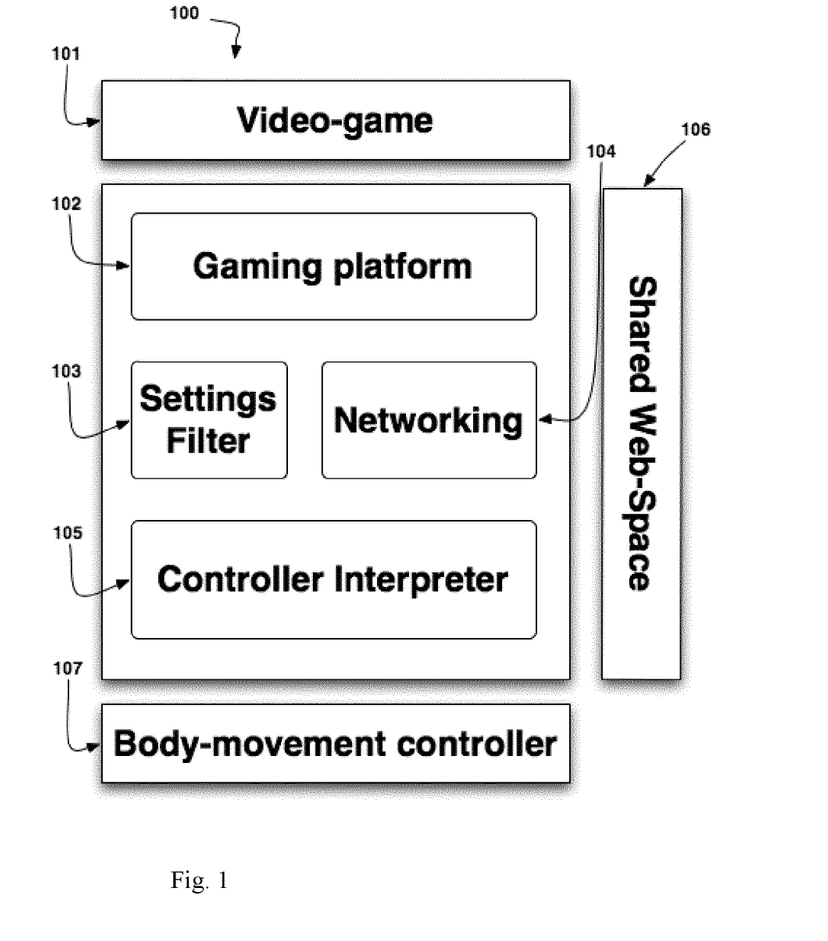
FIG. 1 System components

An embodiment of the proposed invention (100) includes computing means for carrying out the following operations:

Controller Interpreter (105): the controller interpreter is in charge of converting information coming from motion sensing controllers (107) in a readable format for the upper layers. Such information may contain, but are not limited to: amplitude of a movement along each of the three axis; intensity of a movement expressed in speed or acceleration; weight of a part of the body in a specific direction.

Networking (104): the networking component is responsible for communication with the Shared web-space (107). In particular it will gather the last settings imposed by the therapist from the shared web-space as soon as the game starts; furthermore, it will send to the shared web-space aggregated data related to the last game played, in order to be read later by the therapist.

Settings filter (103): this is the module that handles the filtering of data coming from the controller interpreter with the information gathered by the networking from the shared web-space. Here, movements of the patient with motion sensing controller are object of a transformation that will drive the video-game in such a way that patient limits those movements that could be dangerous for his situation.

Gaming platform (102): the gaming platform gets the transformed output of the settings filter and drives a specific video-game (101), by translating movement in command for such video-game. The gaming platform is also in charge of loading the proper video-game for current patient.

Figure 3:
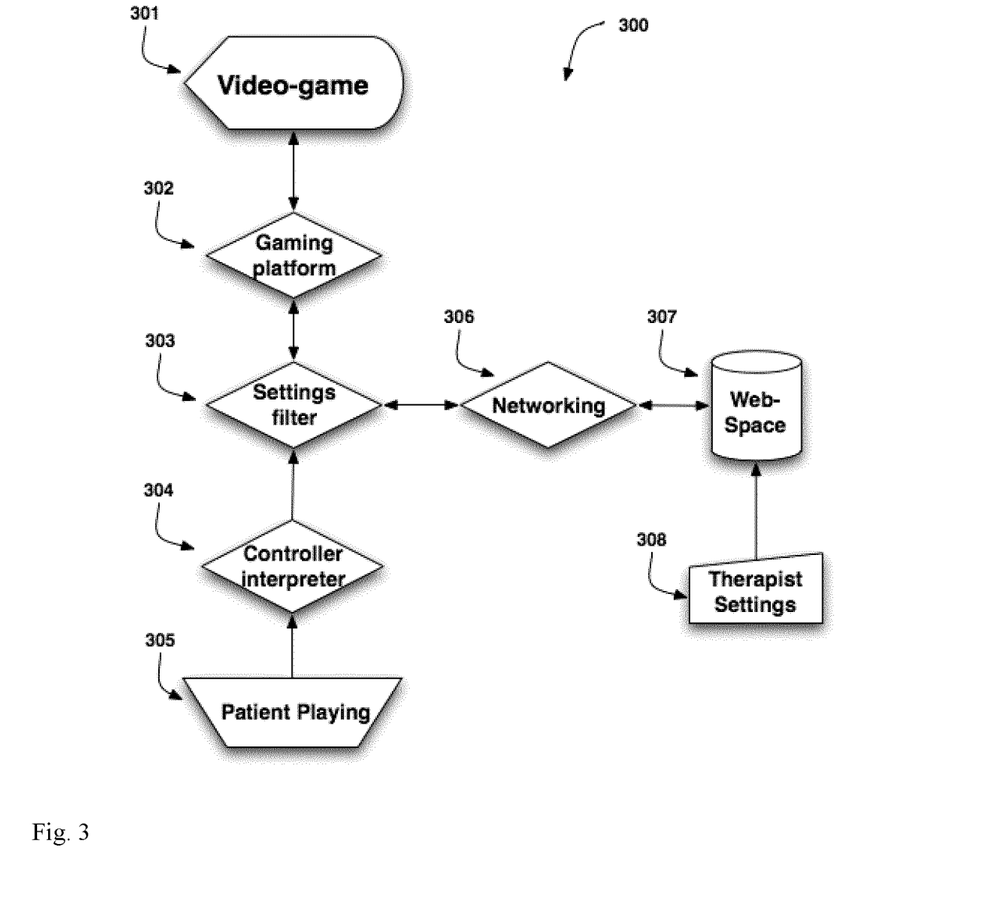

Such components interact among each other to drive a video-game as described in 300. The patient playing (305) creates outputs from the motion-sensing controller he/she is using. Said outputs are read by the Controller Interpreter (304). At the same time, the networking module (306) gathers information from the Web Space (307) where the Therapist (308) has loaded specific settings. The Settings filter (303) gets those information and produces an output readable for the Gaming platform (302). Finally, data drive the Video-game (301).

Figure 2:
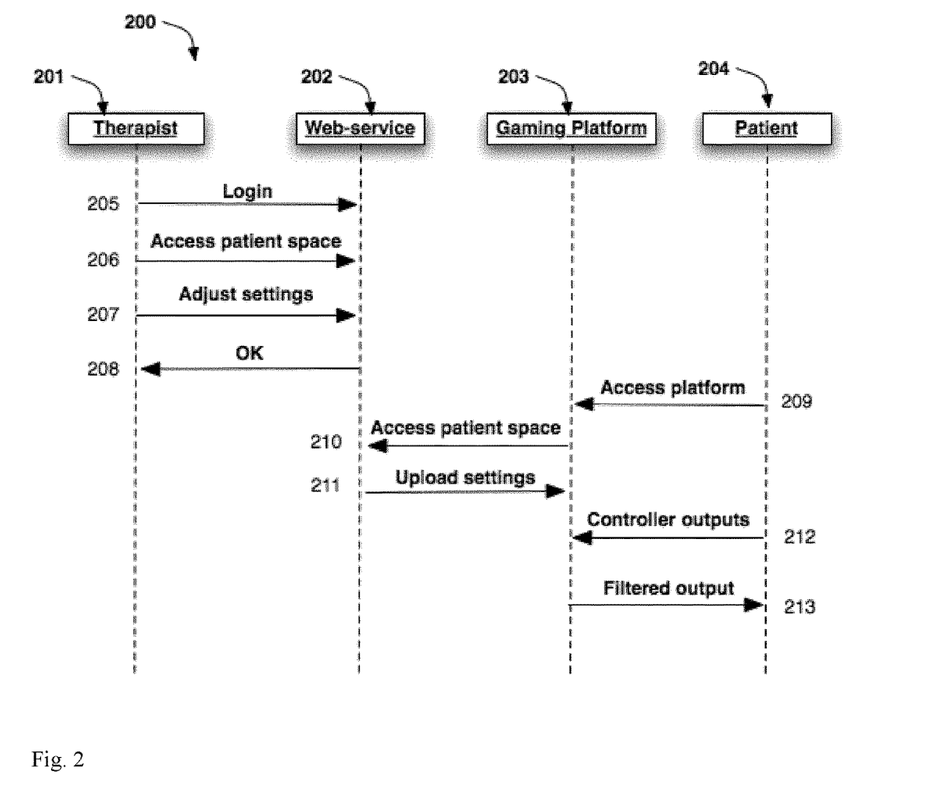
Figure 4:
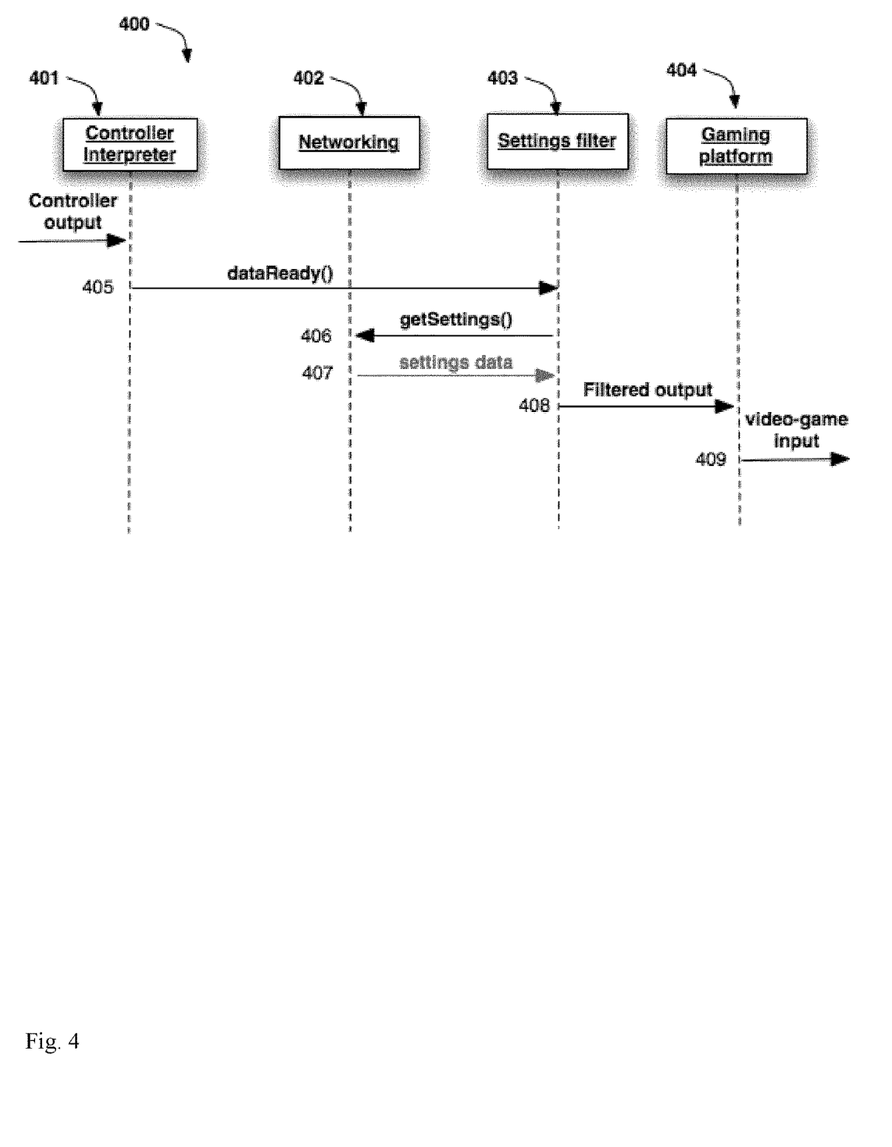

As stated above, one of the main aspects of the invention is related to the way the settings of the therapist are imposed to the patient playing the video-game. In 200, it is shown how the patient (204) and the therapist (201) interact asynchronously through the shared web space (202). At first the therapist makes a login into the shared web space (205) and accesses the patient specific space (206); then, he can adjust the settings (207) through a usable web interface, and receive an ok message of the occurred update (208). After a while, the patient himself starts the rehabilitation exercise with the present invention and the gaming platform (204) accesses the shared web space (209, 210). Settings are then gathered and uploaded onto the gaming platform (211). From this moment on, all the outputs of the controller (212) are filtered by the gaming platform, and a filtered output of the movements is shown, through the game selected by the gaming platform, to the patient (213). FIG. 400 shows more in details the components interaction needed to obtain the filtering of the controller outputs before controlling a game of the gaming platform. In particular, the settings filter (403), as soon as it gets the data ready from the controller interpreter (401), asks the Networking module (402) for the settings data (406, 407), in order to produce the filtered output (408) able to control the gaming platform (404) properly and then produce a correct videogame input (409).

Figure 5:
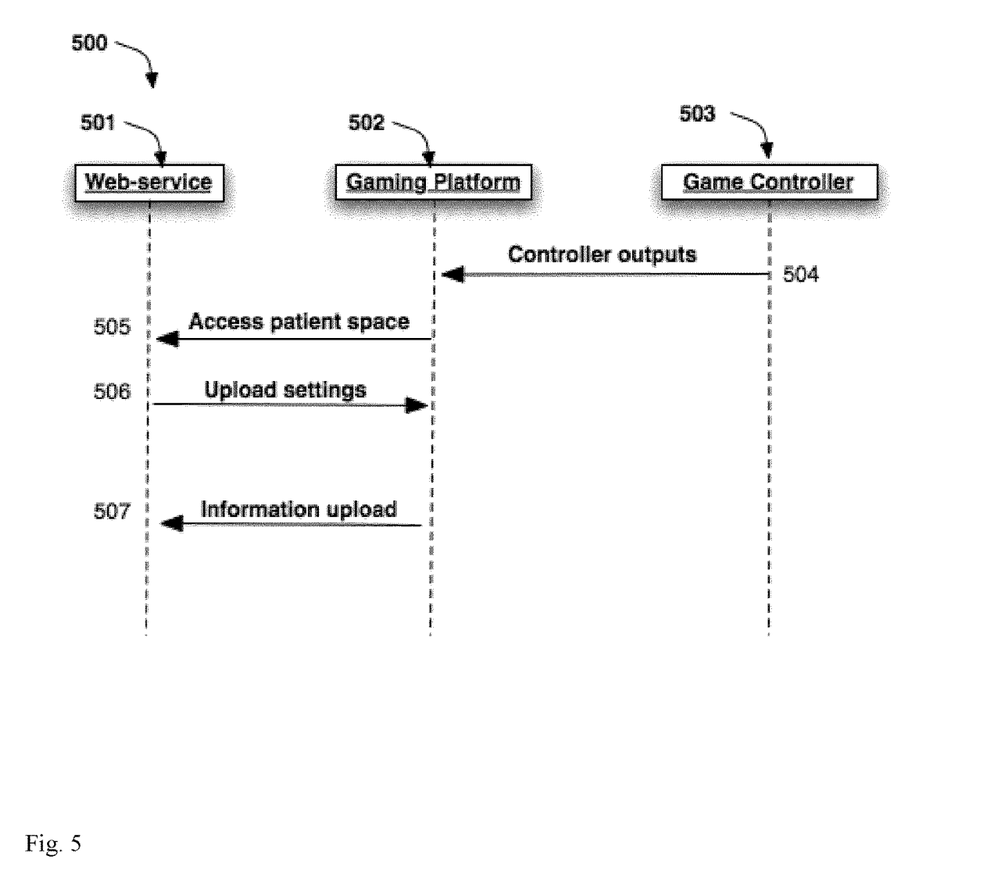

The second aspect of the invention is instead related to the data collected on the shared web space. During the game or at the end of it, data are sent to the web service that analyzes it, correlates it with the personal information of the patient and the settings of the therapist and finally, when the gaming session is over, creates a readable and meaningful report on the done activities. Figure 500 shows how information are uploaded on the web-service (501) after playing with the gaming platform (502). Data coming (504) from the gaming controller (503) represent input of the gaming platform. The gaming platform gathers the therapist settings from the web-service (505, 506) that filters the output of the game controllers. Information are then sent to the web-service (507) either when the game is over or as soon as a bunch of data is ready for analysis by the web-service.

Figure 6:
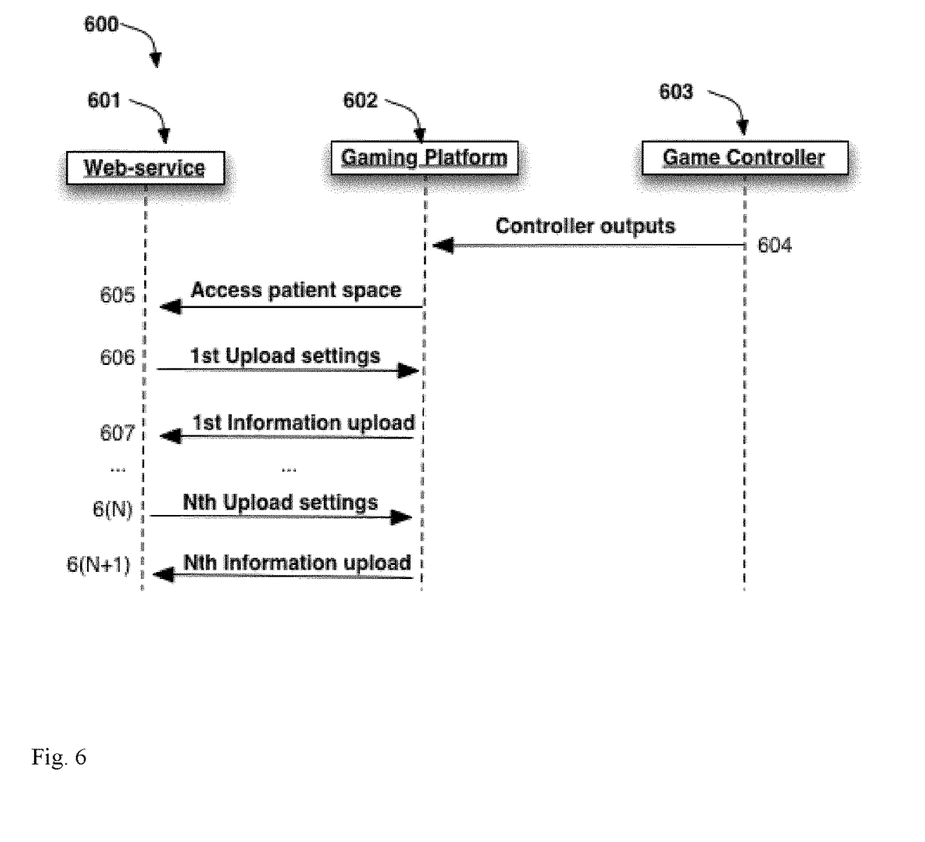

According to a further improvement of this aspect of the invention during the game data are sent (607) to the web service (601) that analyzes it, the settings of the therapist are correlated with preset values information and automatically compared to said preset values, comparison data values are generated. The new comparison of said comparison data values with said preset comparison master data automatically generates new rehabilitation parameters (608) on the basis of the evolution of the rehabilitation therapy. The cycle repeats n times up to a comparison level below a threshold value.

Three specific scenarios are identified to better explain this invention:
1. a patient injured to a leg, using a board able to sense the weight on the injured leg
2. a patient injured to an arm, using a remote controller able to understand the amplitude and the strength of the movement done by the arm
3. a patient with problems on the back, using a combination of a board able to sense movement with respect to equilibrium axis and controllers attached to arms or leg, working simultaneously with the board In the first scenario, the settings of the therapist interfere with the amplitude of the movement of an arm of the patient playing a game, e.g the maximum and the minimum degree for the movement of an arm; when the patient reaches the degree specified as the maximum one, the video-game receives a command such as the patient is at his real maximum degree, or respectively at the real minimum: in such a way, the patient is "forced" to control the movement within the specified range. The intensity and the amplitude of the movements done with the arm are sent to the web server, together with information about the time spent playing.

In the second scenario the settings of the therapist interfere with the amplitude of the movement of bending a leg, when the patient is playing a game, e.g the maximum degree for the bending movement of a leg; when the patient reaches the degree specified as the maximum one, the video-game receives a command such as the patient is at his maximum degree of movement, or respectively at the minimum. While the game is played, information on the bending of the leg are sent to the web-server, again together with the time spent playing.

In the third and final scenario the settings of the therapist specify the maximum weight for the left or right part of the body in correspondence a movement of an arm or a leg, either for upper or lower body. When the patient plays with a balance board controls the video-game by moving his body on top of the balance board itself, in order to turn or move something on the screen left or right. After a proper calibration of the board, the maximum turn is obtained with the maximum weight of the patient moved on that part of the body. If the maximum turn for the left or right part is that specified by the settings imposed for a specific game, the patient has the maximum turn or movement when reaching this threshold. The settings of the therapist specify the maximum weight for the left or right part of the body, either for upper or lower body. When the patient plays with a balance board controls the video-game by moving his body on top of the balance board itself to turn or move something on the screen. The maximum turn is obtained with the maximum weight of the patient moved on that part of the body. If the maximum turn for the left or right part is that specified by the settings imposed for a specific game, the patient has the maximum turn or movement when reaching this threshold. Movements and their intensity are sent to the web service in order to be analyzed and to create a report about the gaming session for the therapist.

The invention claimed is:

1. A method for providing a personalized rehabilitation service to a patient with motion impairments by employing a gaming platform with motion sensing controllers, said method comprising:

employing motion sensing controllers including three dimensional accelerometers, gyroscopes, and weight measurement devices, downloading rehabilitation parameters from a remote server, said parameters being set by a therapist on the basis of the current status of the rehabilitation program of the patient, said parameters are modifying the output of said motion sensors of said gaming platform via a controller to determine a different audio-visual feedback of the gaming platform player movement so that the patient is forced to perform specific movements thanks to the visual feedback of the gaming platform that are the result of a combination of patient movements and therapist parameter settings such that the usability of the game is unaltered by the impaired movement of the patient; said patient controls the correct execution of the rehabilitation exercise by watching and hearing the effect of his movement on the gaming display, while playing the game without limitations on the hardware of said gaming platform and said patient provides updated data related to the rehabilitation session to a remote server for further control of the therapist, wherein:

said updated data from the patient's gaming platform are:
automatically compared to said preset values,
generating comparison data values,
comparing said comparison data values with a preset comparison master data,
and
automatically generating new rehabilitation parameters on the basis of the evolution of the rehabilitation therapy;

wherein said parameters are accessed by the patient and by the therapist for modification via a web interface;

wherein said updated data from the patient's gaming platform are automatically compared to preset values further comprise said values being set on the basis of the evolution of the rehabilitation therapy to automatically generate a report for the therapist;

wherein data from the motion sensing controller are automatically transformed and used as feedback to drive the video-game in such a way to limit patient movements that could be dangerous for the patient's situation; and wherein said patient controls the correct execution of the rehabilitation exercise by watching and hearing the effect of his movement, while playing the game without limitations on the hardware of said gaming platform.

2. An apparatus for providing a personalized rehabilitation service to a patient with motion impairments by employing a gaming platform with motion sensing controllers, said apparatus comprising:

said motion sensing controllers including three dimensional accelerometers, gyroscopes, and weight measurement devices means for downloading rehabilitation parameters from a remote server, means for setting said parameters by a therapist on the basis of the current status of the rehabilitation program of the patent means for modifying the output of said motion sensors of said gaming platform via a controller to determine a different audio-visual feedback of the gaming platform player movement so that the patient is forced to perform specific movements thanks to the audio-visual feedback of the gaming platform that are the result of a combination of patient movements and therapist parameter settings such that the usability of the game is unaltered by the impaired movement of the patient;

means for automatically comparing said updated data from the patient's gaming platform to preset values, means for generating comparison data values, means for accessing said parameters via a web interface for modification by the patient and by the therapist, means for comparing said comparison data values with a preset comparison master data, means for automatically generating new rehabilitation parameters on the basis of the evolution of the rehabilitation therapy;

the gaming platform configured to automatically transform and use data from the motion sensing controller as feedback to drive the video-game in such a way to limit patient movements that could be dangerous for the patient's situation; and a display and a loudspeaker where said patient controls the correct execution of the rehabilitation exercise by watching and hearing the effect of his movement while playing the game without limitations on the hardware of said gaming platform, wherein said updated data from the patient's gaming platform are automatically compared to preset values, said values being set on the basis of the evolution of the rehabilitation therapy to automatically generate a report for the therapist.

3. The apparatus of claim 2, further comprising means for said patient to provide updated data related to the rehabilitation session to a remote server for further control of the therapist.

4. The apparatus of claim 2, comprising means for accessing said parameters via a web interface for modification by the patient and by the therapist.

5. The method of claim 1, wherein said parameters are accessed by the patient and by the therapist for modification via a web interface.

* * * * *